(12) United States Patent
Chenede

(10) Patent No.: US 6,878,842 B2
(45) Date of Patent: Apr. 12, 2005

(54) PROCESS FOR THE ENANTIOSELECTIVE SYNTHESIS OF PROPARGYL ALCOHOL DERIVATIVES OF R CONFIGURATION FROM THE RACEMIC MIXTURES THEREOF

(75) Inventor: Alain Chenede, Vienne (FR)

(73) Assignee: Galderma Research & Development, S.N.C., Valbonne (FR)

( * ) Notice: Subject to any disclaimer, the term of this patent is extended or adjusted under 35 U.S.C. 154(b) by 4 days.

(21) Appl. No.: 10/423,051

(22) Filed: Apr. 25, 2003

(65) Prior Publication Data
US 2004/0049067 A1 Mar. 11, 2004

Related U.S. Application Data
(60) Provisional application No. 60/377,613, filed on May 6, 2002.

(30) Foreign Application Priority Data
Apr. 25, 2002 (FR) ............................................. 02 05220

(51) Int. Cl.$^7$ ............................................... C07C 69/76
(52) U.S. Cl. .......................................... 560/56; 562/466
(58) Field of Search ............................. 560/56; 562/466

(56) References Cited
U.S. PATENT DOCUMENTS
5,716,624 A * 2/1998 Bernardon .................. 424/401

FOREIGN PATENT DOCUMENTS
FR 0661258 * 7/1995
WO WO97/33856 * 9/1997

* cited by examiner

Primary Examiner—Paul J. Killos
(74) Attorney, Agent, or Firm—Burns, Doane, Swecker & Mathis, L.L.P.

(57) ABSTRACT

The invention relates to a novel process for synthesizing organic compounds of general formula (I):

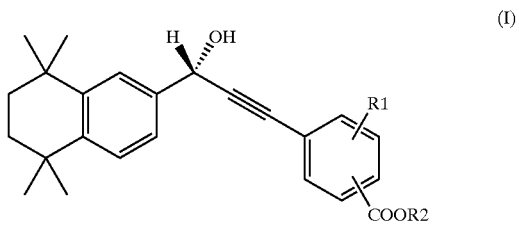

said process may be carried out on an industrial scale and makes it possible to obtain from a mixture of racemic alcohols of formula (II),

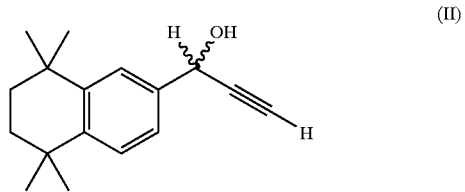

the corresponding chiral alcohols of R configuration, in a high chemical yield.

18 Claims, No Drawings

PROCESS FOR THE ENANTIOSELECTIVE SYNTHESIS OF PROPARGYL ALCOHOL DERIVATIVES OF R CONFIGURATION FROM THE RACEMIC MIXTURES THEREOF

This application claims priority under 35 U.S.C. § 119 to U.S. Provisional Application No. 60/377,613 entitled PROCEDE DE SYNTHESE ENANTIOSELECTIVE DE COMPOSES ORGANIQUES and filed on May 6, 2002, the entire content of which is hereby incorporated by reference.

In the context of the development of novel pharmaceutical active principles containing a chiral centre, it is necessary to have available synthetic processes for obtaining one enantiomeric form from the racemic form.

These processes for preparing enantiomerically pure compounds must have a high chemical yield and also a high enantiomeric excess. The process also needs to be easy to implement on the industrial scale and it must be able to be performed in a minimum number of steps.

The Applicant has now developed a process of enantioselective synthesis, which is easy to carry out on an industrial scale, for obtaining an alcohol of R configuration with a high chemical yield and with excellent chiral purity, an enantiomeric excess of greater than 98%, in a limited number of steps, and especially without a step for isolating the synthetic intermediates.

The invention thus relates to a novel process for the enantioselective synthesis of organic compounds of general formula (I):

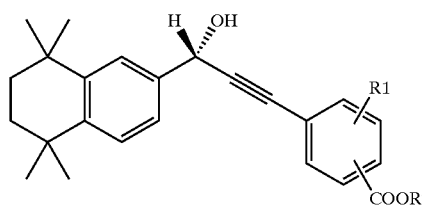

(I)

in which:
  $R_1$ represents a hydrogen atom, an alkyl radical containing from 1 to 6 carbon atoms, an aryl radical, a halogen atom or a radical —$OR_3$, $R_3$ having the meaning given below,
  $R_2$ represents a hydrogen atom or an alkyl radical containing from 1 to 6 carbon atoms,
  $R_3$ represents a hydrogen atom or an alkyl radical containing from 1 to 6 carbon atoms,
said process consisting of a reaction for the stereoselective acylation of a racemic propargyl alcohol in the presence of a lipase, a solvent and an acylating agent, the reaction continuing in the same solvent as the starting solvent, via a Mitsunobu reaction on the mixture of alcohol and acetate.

These two reactions carried out with the same single solvent thus lead, without any step of complex separation of the synthetic intermediates, to the propargyl alcohol of desired configuration after transesterification of the corresponding ester. It is this which gives the reaction its great capacity to be transposed to the industrial scale. The compounds as claimed in the invention are then obtained from the propargyl alcohol of R configuration above by a coupling reaction with suitably substituted aromatic halides, as claimed in the chemical techniques known to those skilled in the art.

The prior art consists of the invention by P. Y-K. Wong et al. described in U.S. Pat. No. 5,447,865, and claiming a chemical or enzymatic resolution and also the recovery of optically pure intermediates, while avoiding the use of chromatography. The authors use an enzymatic reaction but define a process for isolating the compounds obtained by forming complexes of metal salts (lithium salt). Thus, a racemic mixture of cyclopentenones substituted by a hydroxyl group is placed in contact with an effective amount of lipase and an acylating agent, and optionally in the presence of a solvent. The lipase selectively catalyzes the esterification of the alcohol of R configuration, resulting in a mixture of acetate of R configuration and of unreacted alcohol of S configuration. The enzyme in suspension is separated from the mixture by conventional separation techniques, i.e. filtration, centrifugation and decantation. The mixture obtained is treated with a lithium salt, in the presence of a solvent, to form a stable crystalline complex of lithium salt with the S alcohol. The complex obtained is filtered off, the filtrate containing the acetate of R configuration. The alcohol of S configuration is recovered by subjecting the complex to a hydrolytic cleavage under suitable conditions. A Mitsunobu configuration-inversion reaction may be performed on the alcohol of S configuration obtained to give, after transesterification, the alcohol of desired R configuration.

In contrast with the invention, the prior art thus encouraged a person skilled in the art to separate the acetate of desired configuration of the alcohol of R configuration from the unreacted alcohol of S configuration, by producing a complex of the alcohol with metal salts. On reading the prior art, this separation appears to be essential in order to continue the reactions on the two compounds independently and thus to obtain the desired optically pure alcohol. The prior art therefore did not make it possible to deduce the invention in an obvious manner and did not suggest to a person skilled in the art obtaining the compounds of formula (II) by performing the Mitsunobu reaction directly on the mixture obtained at the end of the enzymatic reaction, i.e. the mixture of R acetate and of S alcohol.

The synthetic process as claimed in the invention thus makes it possible to obtain the organic compounds of R configuration of formula (I) below:

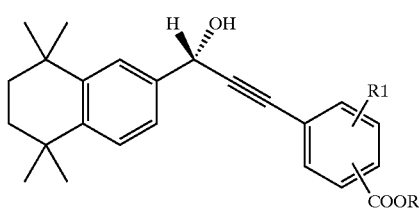

(I)

in which:
  $R_1$ represents a hydrogen atom, an alkyl radical containing from 1 to 6 carbon atoms, an aryl radical, a halogen atom or a radical —$OR_3$, $R_3$ having the meaning given below,
  $R_2$ represents a hydrogen atom or an alkyl radical containing from 1 to 6 carbon atoms,
  $R_3$ represents a hydrogen atom or an alkyl radical containing from 1 to 6 carbon atoms,
said process being noteworthy in that it comprises the following steps:

a) placing a compound of formula (II):

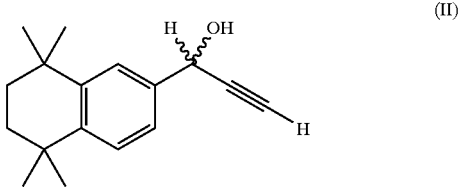

(II)

in contact with an effective amount of lipase in the presence of an acylating agent and a solvent to obtain a mixture of corresponding R acetate and S alcohol, b) treating the mixture of R acetate and S alcohol with a dialkyl azodicarboxylate in the presence of trialkyl or triaryl phosphines and a nucleophilic compound so as to convert the S alcohol into R acetate by inversion of configuration, c) obtaining the corresponding R alcohol by transesterification, in the presence of methanol and sodium carbonate, followed by a crystallization, d) and then coupling the alcohol thus obtained with the compound of formula (III)

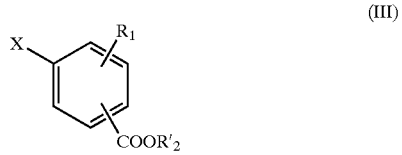

(III)

in which

X represents a halogen atom $R_1$ has the same meaning as above $R'_2$ represents a hydrogen atom or an alkyl radical containing from 1 to 6 carbon atoms, in this latter case, the ester possibly undergoing a saponification reaction to give the compound of formula (I) with $R_2$=H.

During the first step a), the lipase selectively catalyzes the esterification of the alcohol of R configuration, thus producing a mixture of acetate of R configuration and unreacted alcohol of S configuration.

As non-limiting examples of enzymes that may be suitable for the reaction, mention may be made of the lipases derived from pig pancreas, corn germ, *Candida cylindracea, Candida lipolytica, Rhizopus arrhizus, Chromobacterium viscosum, geotichum candidum, Rhizopus delamar*, and lipases obtained from *Pseudomonas*, for instance *Pseudomonas cepacia* and *Pseudomonas fluorescens*. All these enzymes may be obtained commercially from many suppliers, including Sigma Chemicals Co. and Amano Company. The preferred lipase for use in the present invention is lipase PS 30 Amano (lipase from *Pseudomonas cepacia*).

In general, the proportion of lipase required to carry out the enzymatic reaction as claimed in the invention is between 1% and 50% (weight/weight) of racemic mixture, preferably between 10% and 40% and more preferably 20%.

As non-limiting examples of acylating agents used as claimed in the invention, mention may be made of vinyl acetate, vinyl propionate, vinyl butyrate, vinyl valerate, isopropenyl acetate or isopropenyl valerate. The preferred acylating agent is vinyl acetate. The acylating agent as described above may be used in the following ratio: between 0.01 and 20 mol of acylating agent per mole of starting racemic compound, preferably between 0.1 and 5 mol and more preferably 1 mol of acylating agent per mole of racemic compound.

As non-limiting examples of solvents, mention may be made of alkanes, for instance pentane, hexane, heptane and cyclohexane, ethyl acetate, chlorinated alkanes such as methylene chloride, ether solvents, for instance isopropyl ether and tetrahydrofuran (THF), and aromatic solvents, for instance toluene. The acylating agent may also be used as solvent. The solvent preferably used in the reaction as claimed in the invention is heptane. The proportion of solvent required is between 0.1 and 50 volumes of solvent per weight of starting racemic compound, preferably between 1 and 10 volumes/weight and more preferably between 1.5 and 3 volumes/weight.

The enzymatic reaction is performed at a temperature of between 10 and 100° C. and preferably between 35 and 40° C., for a duration of between 10 hours and 10 days, preferably between 1 and 2 days. The mixture is stirred during the reaction time by conventional stirring means including mechanical stirring.

Thereafter, the enzyme in suspension is filtered from the reaction mixture containing the acetate of desired R configuration and the alcohol of S configuration using conventional techniques including filtration, centrifugation or decantation, and more preferably filtration.

The second step consists of the Mitsunobu reaction, intended to produce the inversion of configuration of the S alcohol and to convert it into acetate of R configuration. It is performed directly on the mixture of R acetate and S alcohol obtained from the first step, without changing the solvent, and without a step for separating the two compounds, the R ester remaining inert under the conditions defined as claimed in the invention. A dialkyl azodicarboxylate and trialkyl or triaryl phosphines are added to the preceding reaction mixture, in the solvent, in the presence of a nucleophile, in order to produce the intermediate oxyphosphonium complex allowing, by reaction with the alcohol, the desired inversion of configuration.

As non-limiting examples of dialkyl azodicarboxylates, mention may be made of diethyl azodicarboxylate (DEAD) and diisopropyl azodicarboxylate (DIAD). DIAD will preferably be used to perform the Mitsunobu reaction as claimed in the invention. The proportion of dialkyl azodicarboxylate required to carry out the reaction is between 0.01 and 50 mol of reactant per mole of starting mixture, preferably between 0.1 and 5 mol and more preferably 0.5 mol.

As non-limiting examples of trialkyl or triaryl phosphines, mention may be made of triphenylphosphine (TPP) and tri-n-butylphosphine (TBP). TBP will preferably be used to perform the Mitsunobu reaction as claimed in the invention. The proportion of trialkyl or triaryl phosphine required to carry out the reaction is between 0.01 and 50 mol of reagent per mole of starting mixture, preferably between 0.1 and 5 mol and more preferably 0.5 mol.

As non-limiting examples of nucleophilic compounds, mention may be made of carboxylic acids, such as acetic acid, propionic acid, butyric acid and valeric acid, and more generally alkanoic acids; acetic acid will preferably be used, most particularly when the acylating agent is vinyl acetate. The proportion of nucleophilic compound required to carry out the reaction is between 0.01 and 50 mol of reagent per mole of starting mixture, preferably between 0.5 and 5 mol and more preferably 0.5 mol.

The reagents cooled to a temperature of between −5 and 20° C., preferably to a temperature below 5° C., are added to the mixture of acetate and alcohol in the solvent, also cooled to between −5 and 5° C., and preferably to 0° C. The mixture is then heated to a temperature of between 10 and 30° C., preferably between 17 and 23° C., and maintained at this temperature for a time of between 1 and 10 hours and preferably for 2 hours 45 minutes.

Advantageously, the phosphine oxide and DIAD derivative obtained as by-products of the reaction along with the ester of R configuration must be removed so as not to interfere in the rest of the reaction, with the crystallization of the R alcohol, by conventional techniques such as chromatography or liquid/liquid extraction and preferably by liquid/liquid extraction. Liquid/liquid extraction is a reaction that is easy to carry out and effective as claimed in the invention. Preferably, the liquid/liquid extraction will be performed continuously. Non-limiting examples of solvents used in the context of this continuous extraction are heptane, methanol and water. Heptane and an ethanol/water mixture (85/15) in an extraction/back-extraction system will preferably be used. The solvents are used in proportions ranging between 1 and 50 volumes per volume of starting reaction mixture, and preferably between 15 and 25 volumes. The liquid/liquid extraction takes place at a temperature of between 10 and 25° C. and preferably at 20° C., for a time of between 10 minutes and 2 hours, preferably for 1 hour.

The transesterification of the R ester makes it possible to obtain, after crystallization, the alcohol of chosen R configuration. The transesterification is performed in the presence of an alcohol, a base and a solvent, or preferably in the presence of an alcoholic solvent and a base. The mixture is heated to between 30 and 70° C., preferably to 45° C., for a time of between 5 and 30 hours, preferably for 15 hours. After washing with water, the crystallization is performed by cooling the organic phase to a temperature below 0° C., preferably to −5° C., for a time of between 10 minutes and 1 hour, preferably for 30 minutes.

As non-limiting examples of bases used for the transesterification reaction, mention may be made of sodium carbonate, potassium carbonate, sodium hydroxide and alumina. The base preferably used as claimed in the invention is sodium carbonate. The proportion of base required to carry out the reaction is between 0.01 and 50 mol of base per mole of starting reaction mixture, preferably between 0.1 and 5 mol and more preferably 2 mol.

As non-limiting examples of solvents used for the transesterification reaction, mention may be made of alcoholic solvents such as methanol, ethanol and isopropanol. The alcoholic solvent preferably used as claimed in the invention is methanol. The proportion of solvent required to carry out the reaction is between 1 and 50 volumes of solvent per weight of starting reaction mixture, preferably 5 volumes.

The overall chemical yield for the production of the alcohol of formula (II) of R configuration from the racemic mixture of formula (II) is preferably greater than 50%, and the chiral purity of the alcohol obtained is preferably greater than 99%.

The invention relates especially to a synthetic process as defined above, wherein the lipase used during step a) is chosen from lipases obtained from *Pseudomonas*; the lipase is preferably *Pseudomonas cepacia* lipase.

The invention relates especially to a synthetic process as defined above, wherein the acylating agent used in step a) is chosen from vinyl acetate, vinyl propionate, vinyl butyrate and vinyl valerate, and the acylating agent is preferably vinyl acetate.

The invention relates especially to a synthetic process as defined above, wherein the solvent used in a) is chosen from alkanes, for instance pentane, hexane, heptane and cyclohexane, ethyl acetate, chlorinated alkanes such as methylene chloride, ether solvents, for instance isopropyl ether and tetrahydrofuran, and aromatic solvents, for instance toluene, and the solvent is preferably heptane.

The invention relates especially to a synthetic process as defined above, wherein the dialkyl azodicarboxylate used in step b) is chosen from diethyl azodicarboxylate and diisopropyl azodicarboxylate, and the dialkyl azodicarboxylate is preferably diisopropyl azodicarboxylate.

The invention relates especially to a synthetic process as defined above, wherein the trialkyl or triaryl phosphine used in step b) is chosen from triphenylphosphine and tri-n-butylphosphine, and the trialkyl or triphenyl phosphine is preferably tri-n-butylphosphine.

The invention relates especially to a synthetic process as defined above, wherein the nucleophilic compound used in step b) is chosen from carboxylic acids, and the carboxylic acid is preferably acetic acid.

The process as claimed in the invention is especially noteworthy in that step a) is performed at a temperature of between 10 and 100° C., and preferably at a temperature of between 35 and 40° C.

The process as claimed in the invention is especially noteworthy in that step a) is performed for a duration of between 10 hours and 10 days and preferably for a duration of between 1 and 2 days.

The invention also relates to a process, which may be carried out on an industrial scale, for synthesizing propargyl alcohol of formula (Ia):

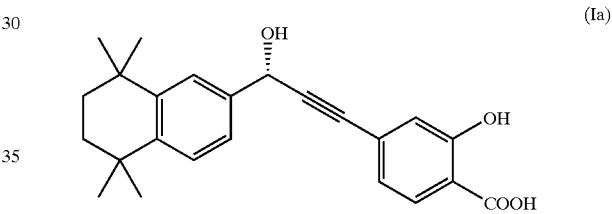

(Ia)

said process being noteworthy in that it comprises the following steps:

a) placing a compound of formula (IIa):

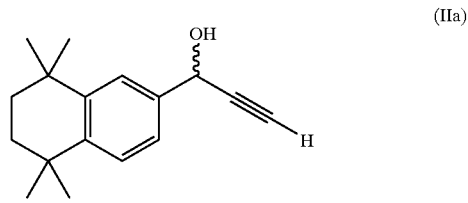

(IIa)

in contact with an effective amount of lipase obtained from *Pseudomonas* in the presence of vinyl acetate as acylating agent and heptane as solvent, to form the corresponding R acetate and S alcohol;

b) treating the mixture of R acetate and S alcohol with diisopropyl azodicarboxylate in the presence of tri-n-butylphosphine and acetic acid so as to obtain the R acetate by inversion of configuration of the S alcohol;

c) obtaining the optically pure corresponding R alcohol, by transesterification, in the presence of methanol and sodium carbonate, followed by a crystallization;

d) coupling, via a standard chemical reaction, the alcohol with the compound of formula (IIIa) below:

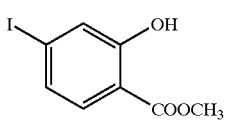

and performing a saponification reaction to obtain the compound of formula (Ia):

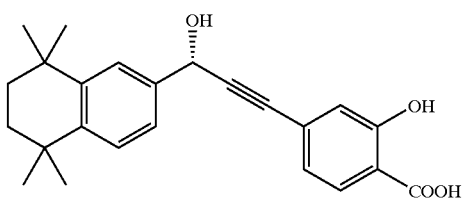

The process as claimed in the invention is also noteworthy in that the overall chemical yield for the three steps a, b and c is preferably 60% and in that the chiral purity of the alcohol obtained is greater than 98% and preferably equal to 99%.

A non-limiting example of implementation of the process as claimed in the invention will now be given for indicative purposes.

EXAMPLE 1

Preparation of S-(+)-2-hydroxy-4-[3-hydroxy-3-(5,6,7,8-tetrahydro-5,5,8,8-tetramethyl-2-naphthyl)-1-propynyl]benzoic acid from 1-(5,6,7,8-tetrahydro-5,5,8,8-tetramethyl-2-naphthyl)prop-2-yn-1-ol

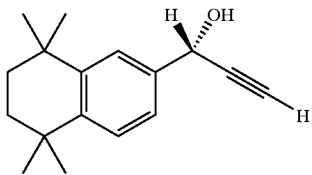

The compound 1-(5,6,7,8-tetrahydro-5,5,8,8-tetramethyl-2-naphthyl)prop-2-yn-1-ol (31.0 kg) is placed in contact with lipase PS 30 Amano (6.2 kg) and vinyl acetate (11.0 kg) at a temperature below 40° C., in the presence of heptane (47 liters).

The mixture is heated at a temperature of about 36 to 40° C. for 33 hours with mechanical stirring. The mixture is then cooled to a temperature of about 25/30° C.

The enzyme in suspension is then filtered from the reaction mixture containing the acetate of desired R configuration and the alcohol of S configuration. The mixture is heated again to 40/50° C. so as to evaporate to constant volume, by adding heptane, the majority of the solvents and reagents. A mixture of 33 kg of alcohol of S configuration and of acetate of R configuration dissolved in the heptane is thus obtained.

10 liters of heptane cooled to 0/−5° C. are added to the solution of S alcohol and R acetate obtained above, and 14.3 kg of tri-n-butylphosphine (TBP) are added at a temperature below 25° C., in the presence of 4.22 kg of 99% acetic acid at a temperature below 7° C. The mixture is cooled to 0/5° C., followed by addition of 14.5 kg of diisopropyl azodicarboxylate (DIAD) at a temperature below 5° C. The mixture is then heated to a temperature of about 20° C. and maintained at this temperature for 2 hours 45 minutes.

The phosphine oxide and the DIAD derivative obtained along with the acetate of desired configuration are removed by liquid-liquid extraction (2 extractions with 5 volumes of methanol/water mixture (85:15), then 2 back-extractions with 5 volumes of heptane, and then 1 extraction with 5 volumes of methanol/water (85:15)).

The transesterification of the R acetate is performed in the presence of sodium carbonate (27.1 kg) and methanol (155 liters), by heating the mixture at 40° C. for 7 hours 15 minutes. After adding a heptane/water mixture (50:50), the reaction mixture is again heated to 60/65° C. to remove the methanol by distillation.

After separation of the organic and aqueous phases, the crystallization is performed by cooling the organic layer obtained to the point of crystallization and then maintaining it at a temperature below −5° C. for 30 minutes. After filtration followed by drying for about 11 hours at a maximum temperature of 30° C., the R(−) enantiomer of 1-(5,6,7,8-tetrahydro-5,5,8,8-tetramethyl-2-naphthyl)prop-2-yn-1-ol (18.4 kg) is obtained.

The overall chemical yield for the production of this alcohol of R configuration from the racemic mixture is 60% and the chiral purity of the compound is 99%.

S-(+)-2-Hydroxy-4-[3-hydroxy-3-(5,6,7,8-tetrahydro-5,5,8,8-tetramethyl-2-naphthyl)-1-propynyl]benzoic acid below:

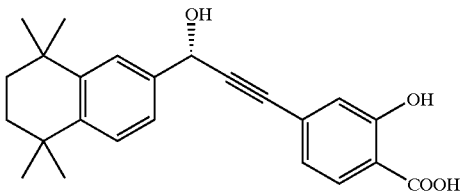

is obtained after coupling R-(−)-1-(5,6,7,8-tetrahydro-5,5,8,8-tetramethyl-2-naphthyl)prop-2-yn-1-ol with methyl iodosalicylate in triethylamine in the presence of Pd(PPh$_3$)$_2$Cl$_2$ and copper iodide, followed by saponification, in THF, of the ester obtained in the presence of lithium hydroxide, and then acidification with HCl.

What is claimed is:

1. Process for synthesizing organic compounds of R configuration of general formula (I):

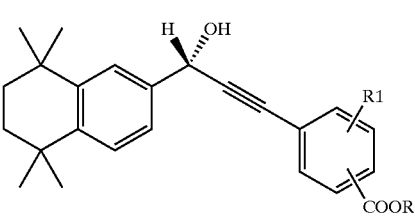

in which:

R$_1$ represents a hydrogen atom, an alkyl radical containing from 1 to 6 carbon atoms, an aryl radical, a halogen atom or a radical —OR$_3$, R$_3$ having the meaning given below, R$_2$ represents a hydrogen atom or an alkyl radical containing from 1 to 6 carbon atoms, R$_3$ represents a hydrogen atom or an alkyl radical containing from 1 to 6 carbon atoms, said process being characterized in that it comprises the following steps:

a) placing a compound of formula (II):

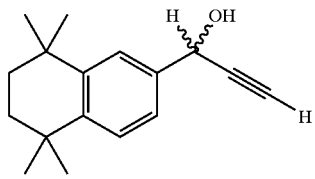

in contact with an effective amount of lipase in the presence of an acylating agent and a solvent to obtain a mixture of corresponding R acetate and S alcohol, b) treating the mixture of R acetate and S alcohol with a dialkyl azodicarboxylate in the presence of trialkyl or triaryl phosphines and a nucleophilic compound so as to convert the alcohol into R acetate by inversion of configuration, c) obtaining the corresponding R alcohol by transesterification, in the presence of methanol and sodium carbonate, followed by a crystallization, and then d) coupling the alcohol thus obtained with the compound of formula (III):

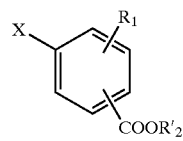

in which:

X represents a halogen atom, $R_1$ has the same meaning as above, $R_2$ represents a hydrogen atom or an alkyl radical containing from 1 to 6 carbon atoms, in this latter case, the ester possibly undergoing a saponification reaction to give the compound of formula (I) with $R_2$=H.

2. Process according to claim 1, characterized in that the lipase is chosen from lipases obtained from *Pseudomonas*.

3. Process according to claim 1, characterized in that the lipase is *Pseudomonas capacia* lipase.

4. Process according to claim 1, characterized in that the acylating agent is chosen from vinyl acetate, vinyl propionate, vinyl butyrate, and vinyl valerate.

5. Process according to claim 1, characterized in that the acylating agent is vinyl acetate.

6. Process according to claim 1, characterized in that the solvent is chosen from alkanes, ethyl acetate, chlorinated alkanes, ether solvents, and aromatic solvents.

7. Process according to claim 1, characterized in that the solvent is heptane.

8. Process according to claim 1, characterized in that the dialkyl azodicarboxylate is chosen from diethyl azodicarboxylate and diisopropyl azodicarboxylate.

9. Process according to claim 1, characterized in that the dialkyl azodicarboxylate is diisopropyl azodicarboxylate.

10. Process according to claim 1, characterized in that the trialkyl or triaryl phosphine is chosen from triphenylphosphine and tri-n-butylphosphine.

11. Process according to claim 1, characterized in that the trialkyl or triaryl phosphine is tri-n-butylphosphine.

12. Process according to claim 1, characterized in that the nucleophilic compound is chosen from carboxylic acids.

13. Process according to claim 1, characterized in that the nucleophilic compound is acetic acid.

14. Process according to claim 1, characterized in that step a) is performed at a temperature of between 10 and 100° C.

15. Process according to claim 1, characterized in that step a) is performed at a temperature of between 35 and 40° C.

16. Process according to claim 1, characterized in that step a) is performed for a duration of between 10 hours and 10 days.

17. Process according to claim 1, characterized in that step a) is performed for a duration of between 1 and 2 days.

18. Process according to claim 1, for the synthesis of propargyl alcohols of R configuration and of formula (Ia) below:

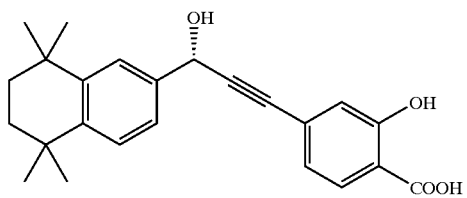

said process being characterized in that it comprises the following steps:

a) placing a compound of formula (IIa):

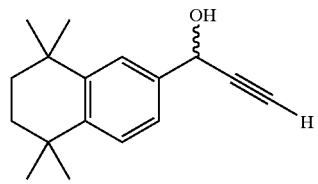

in contact with an effective amount of lipase obtained from *Pseudomonas* in the presence of of vinyl acetate as acylating agent and heptane as solvent, to form the corresponding R acetate and S alcohol;

b) treating the mixture of R acetate and S alcohol with a diisopropyl azodicarboxylate in the presence of tri-n-butylphosphine and acetic acid so as to obtain the R acetate by inversion of configuration of the S alcohol;

c) obtaining the optically pure corresponding R alcohol by transesterification in the presence of methanol and sodium carbonate, followed by a crystallization;

d) coupling, via a standard chemical reaction, the compound of formula (IIIa) below; and
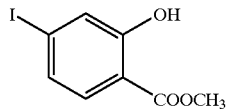
(IIIa)
e) performing a saponification reaction to obtain the compound of formula (Ia):
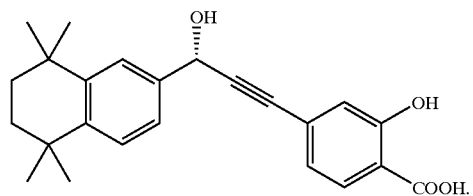
(Ia)
* * * * *